(12) United States Patent
Wilk et al.

(10) Patent No.: US 10,865,959 B2
(45) Date of Patent: Dec. 15, 2020

(54) REFLECTOR FOR PROVIDING UNIFORM LIGHT ENERGY

(71) Applicant: Xenon Corporation, Wilmington, MA (US)

(72) Inventors: Stephen R. Wilk, Saugus, MA (US); Saad Ahmed, Wilmington, MA (US)

(73) Assignee: Xenon Corporation, Wilmington, MA (US)

( * ) Notice: Subject to any disclaimer, the term of this patent is extended or adjusted under 35 U.S.C. 154(b) by 0 days.

(21) Appl. No.: 16/404,138

(22) Filed: May 6, 2019

(65) Prior Publication Data

US 2019/0338919 A1 Nov. 7, 2019

Related U.S. Application Data

(60) Provisional application No. 62/667,136, filed on May 4, 2018.

(51) Int. Cl.
*F21V 7/08* (2006.01)
*F21V 7/00* (2006.01)
*F21V 7/05* (2006.01)

(52) U.S. Cl.
CPC .............. *F21V 7/08* (2013.01); *F21V 7/0016* (2013.01); *F21V 7/05* (2013.01)

(58) Field of Classification Search
CPC ............. F21V 7/08; F21V 7/0016; F21V 7/05
See application file for complete search history.

(56) References Cited

U.S. PATENT DOCUMENTS

| | | | |
|---|---|---|---|
| 4,264,947 A | 4/1981 | Garbe | |
| 4,839,522 A | 6/1989 | Bourgeois et al. | |
| 5,502,310 A | 3/1996 | Niestrath et al. | |
| 6,030,086 A | 2/2000 | Thomas | |
| 2003/0148024 A1 | 8/2003 | Kodas et al. | |
| 2012/0003398 A1 | 1/2012 | Kaszuba et al. | |
| 2014/0231671 A1 | 8/2014 | Lu et al. | |
| 2015/0028020 A1 | 1/2015 | Childers | |
| 2017/0197001 A1 | 7/2017 | Shito | |

OTHER PUBLICATIONS

International Search Report and Written Opinion dated Jul. 29, 2019, in the International Application No. PCT/US19/30886, 18 pages.

*Primary Examiner* — Nicole M Ippolito
*Assistant Examiner* — Hanway Chang
(74) *Attorney, Agent, or Firm* — Wilmer Cutler Pickering Hale and Dorr LLP

(57) ABSTRACT

Systems are disclosed for providing ultraviolet (UV) energy to items on a processing surface. The system includes a lamp positioned over the processing surface to provide UV energy to the processing surface and a reflector cell positioned to cause UV energy emitted from the lamp in a direction away from the processing surface to be reflected toward the processing surface. The system includes the reflector cell having a reflector cap positioned above the lamp and a shroud extending downwardly from the reflector cap toward the conveyor wherein the shroud has a vertical dimension, a longitudinal dimension, and a horizontal dimension along the direction of the conveyor such that the horizontal dimension and the longitudinal dimension define a treatment area on the conveyor. The lamp is configured to deliver energy to the treatment area such that the delivered energy to the processing surface is substantially uniform over the treatment area.

21 Claims, 7 Drawing Sheets

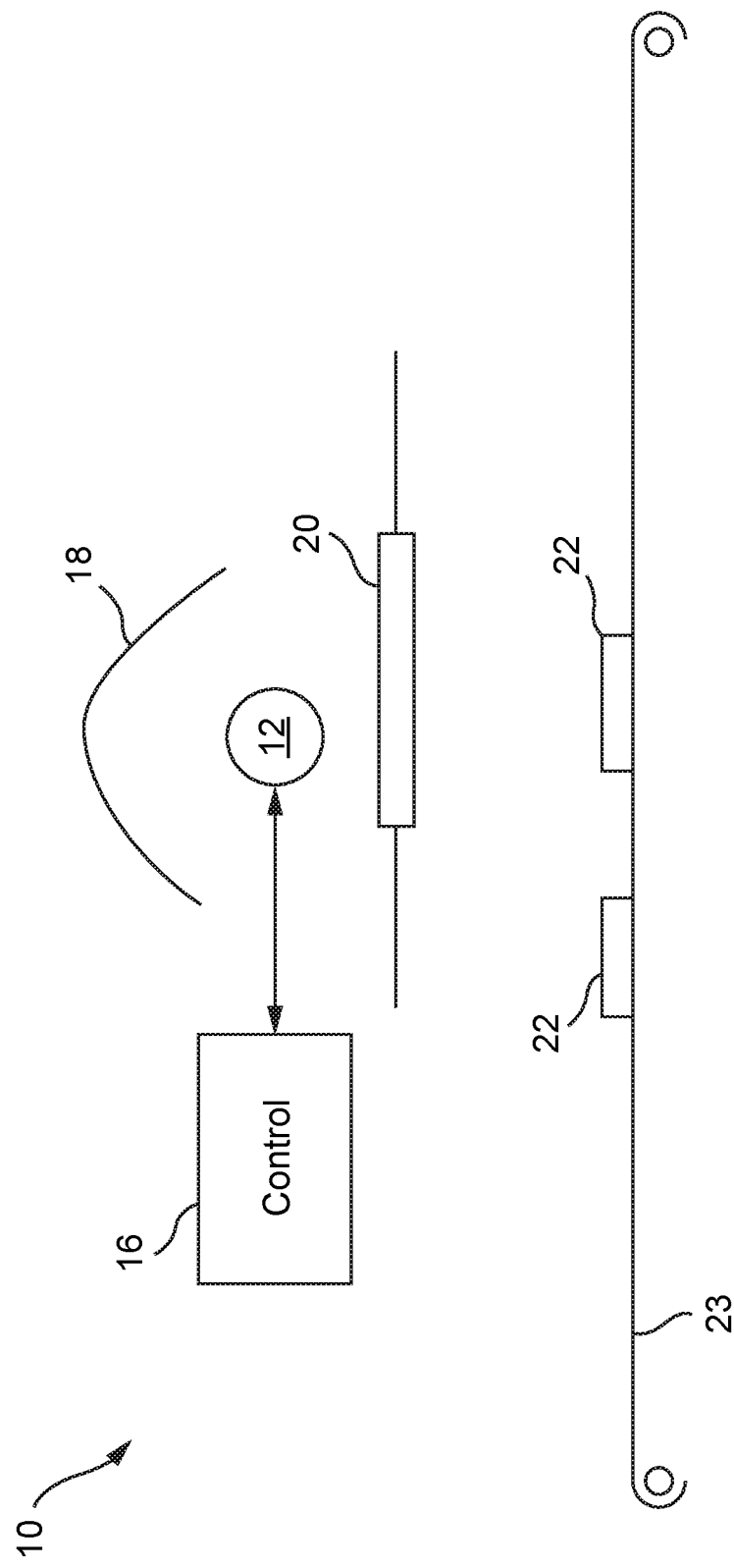

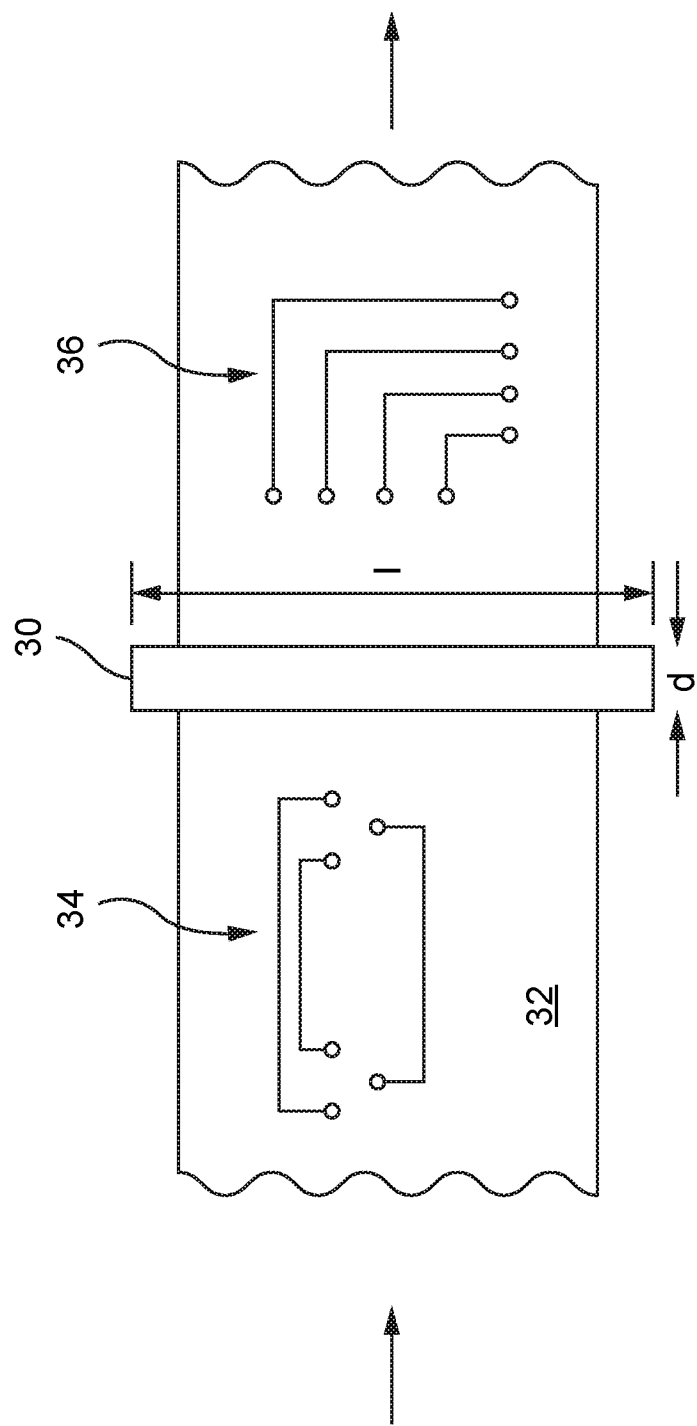

REFLECTOR FOR PROVIDING UNIFORM LIGHT ENERGY

CROSS REFERENCE TO RELATED APPLICATIONS

This application claims priority to U.S. Provisional Application No. 62/667,136, filed May 4, 2018, entitled "Reflector for Providing Uniform Light Energy," the contents of which are incorporated herein in their entirety.

TECHNICAL FIELD

The present disclosure relates generally to light systems, and in particular, to systems and methods for providing uniform UV light to a surface area.

BACKGROUND

In some systems for providing UV light to a target item, a UV lamp is housed in an envelope and emits UV light that is provided to items to be treated, in some cases through a UV-transparent fused silica window, often referred to as quartz. In one type of system, a conveyor belt brings items to be radiated to a xenon flash lamp system, and one or more flash lamps provides one or more flashes of broadband light to the items to be treated. The UV treatment can be used for different purposes, such as curing an adhesive, annealing, or deactivating microorganisms.

SUMMARY OF THE INVENTION

The present disclosure includes a system for providing ultraviolet (UV) energy to items on a processing surface that includes a lamp positioned over the processing surface to provide UV energy to the processing surface and a reflector cell positioned to cause UV energy emitted from the lamp in a direction away from the processing surface to be reflected toward the processing surface. In some embodiments, the reflector cell includes a reflector cap positioned above the lamp and a shroud extending downwardly from the reflector cap toward the conveyor. In some embodiments, the shroud has a vertical dimension, a longitudinal dimension, and a horizontal dimension along the direction of the conveyor whereby the horizontal dimension and the longitudinal dimension defining a treatment area on the conveyor. In some embodiments, the lamp is configured to deliver energy to the treatment area and the reflector cap, and the shroud are configured such that the delivered energy to the processing surface is substantially uniform over the treatment area.

In some embodiments, the system's lamp includes at least one flash lamp and the energy in the treatment area is substantially uniform to within 5%. In some embodiments of the system, the processing surface is defined by a conveyor. In some embodiments, the reflector cap and the shroud define and enclose a treatment volume. In some embodiments, the reflector cap and the shroud have a reflective material along their respective interior surfaces facing the treatment area. In some embodiments, the reflector cap includes a first panel and a second panel, and the first panel and the second panel extend upwardly away from the processing surface and at about a positive and negative 45 degree angle, respectively, relative to the processing surface. In some embodiments, the first and second panels intersect above the lamp such that an angle between the first panel and the second panel is approximately 90 degrees. In some embodiments, the lamp includes a first lamp and a second lamp spaced apart, wherein the first and second panels extend over the first lamp. In some embodiments, the system further includes a third panel and a fourth panel whereby the third panel and the fourth panel extend upwardly away from the processing surface and at about a positive and negative 45 degree angle, respectively, relative to the processing surface. In some embodiments, the third and fourth panels intersect above the second lamp such that an angle between the third panel and the fourth panel is approximately 90 degrees.

In some embodiments of the system, the reflector cap includes a first elliptical shape defining a portion of a first ellipse with a major axis along a first line parallel to the processing surface and perpendicular to a second line from the lamp to the processing surface. In some embodiments, the lamp is positioned at a first focus of the ellipse, and a second focus of the ellipse being spaced from the first focus along the first line. In some embodiments, the reflector cap includes a second elliptical shape defining a portion of a second ellipse with a major axis along the first line whereby the second ellipse has a first focus co-located with the first focus of the first ellipse, and a second focus of the ellipse being spaced from the first focus and from the second focus of the first ellipse along the first line. In some embodiments, the reflector cap includes an elliptical portion defining an ellipse having a major axis perpendicular to the processing surface. In some embodiments, the lamp is positioned at a first focus of the ellipse, and the system includes a second focus below the first focus such that the shroud has a parabolic shape with a focus co-located with the second focus of the reflector cap. In some embodiments, the system further includes a UV-transmissive window positioned between the lamp and the processing surface.

In some embodiments, the system includes at least one ultraviolet (UV) energy lamp positioned above a processing surface, wherein the plane of the processing surface defines a first direction, and the direction from the lamp to the conveyor is a second direction perpendicular to the first direction. In some embodiments, the system includes a reflector cell positioned to cause UV energy emitted from the lamp in a direction away from the processing surface to be reflected toward the processing surface. In some embodiments, the reflector cell includes a reflector cap positioned above the flash lamp and away from the processing surface where the reflector cap has first and second planar panels that extend away from the processing surface at an angle relative to the second direction and meet at a location above the lamp and form a V-shaped cross section. In some embodiments, the system includes a shroud having at least a third panel extending downwardly from the first panel toward the conveyor, and a fourth panel extending toward the processing surface and parallel to the third side such that the lamp provides energy to the processing surface in a treatment area below the first and second sides and bounded by the third and fourth panels.

In some embodiments, the lamp includes a flash lamp. In some embodiments, the reflector cap and the shroud define a treatment volume and the reflector cap and the shroud include a reflective material along interior surfaces facing the treatment volume. In some embodiments, the first and second panels intersect such that the V-shape is approximately 90 degrees. In some embodiments, the processing surface includes a conveyor and the system further includes a UV-transmissive window positioned between the lamp and the conveyor. In some embodiments, the system includes a second lamp and a second reflector cap having fifth and sixth planar panels that that extend away from the processing surface at an angle relative to the second direction and meet at a location above the lamp and form a second V-shaped cross section. In some embodiments, the fourth panel extends downwardly from the second panel, such that the first, second, third, and fourth panels define a home plate shape in cross-section.

In some embodiments, the system includes at least one ultraviolet (UV) energy lamp positioned above a planar processing surface, wherein a direction from the lamp to the processing surface is a first direction perpendicular to the processing surface. In some embodiments, the system includes a reflector cell positioned to cause UV energy emitted from the lamp in a direction away from the processing surface to be reflected toward the processing surface. In other embodiments, the reflector cell includes a reflector cap positioned above the flash lamp and away from the processing surface, wherein the reflector cap includes a first elliptical portion that defines a first elliptical shape with a major axis parallel to the processing surface and perpendicular to the first direction. In some embodiments, the lamp is located at one focus of the first elliptical shape, and a second focus of the first elliptical shape is spaced from the first focus along the second direction. In some embodiments, the system includes a shroud extending from the reflector cap toward the processing surface.

In some embodiments, the system includes a second elliptical portion that defines a second elliptical shape having a major axis co-linear with the major axis of the first elliptical shape. In some embodiments, the lamp is located at a first focus of the second elliptical shape, and a second focus of the second elliptical shape is spaced from both foci of the first elliptical shape. In some embodiments, the shroud includes first and second panels that are spaced apart and extend from the reflector cap toward the processing surface. In some embodiments, the spacing of the first and second panels defines a dimension of a treatment area for the UV energy.

These and other capabilities of the disclosed subject matter will be more fully understood after a review of the following figures, detailed description, and claims. It is to be understood that the phraseology and terminology employed herein are for the purpose of description and should not be regarded as limiting.

BRIEF DESCRIPTION OF THE DRAWINGS

FIG. 1 is a system diagram of a system for treating items using a flash lamp system with a UV-transmissive window, according to some embodiments of the present disclosure.

FIG. 2 is a plan view of a system for treating circuit components using a single-cell flash lamp system, according to some embodiments of the present disclosure.

DETAILED DESCRIPTION

Figure 3A:
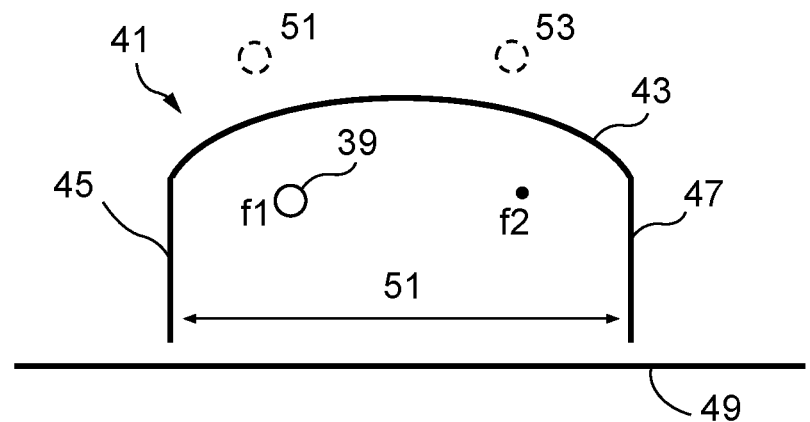
FIG. 3a is a side view of a system for treating items using a flash lamp system with a flash lamp reflector cell having an elliptical reflector cap, according to some embodiments of the present disclosure.

In some applications of UV energy, e.g., sintering traces of conductive lines with nanoparticles, it can be useful to have a large coverage area with known uniform energy being delivered. The systems and methods described here are for reflector systems that provide substantially uniform UV energy over a large area. As used herein, both "UV energy" and "light" are used to describe the output of a lamp system in varying embodiments of the present disclosure.

The system is described here in the context of a UV flash lamp system, such as systems provided by Xenon Corporation, Wilmington Mass., but could be used in a continuous light UV system with one or more mercury lamps, or in other types of light systems.

Such systems often have a reflector positioned such that the light source is between the reflector and the items to be treated. The reflector directs UV light energy toward the items to be treated. Some reflector configurations are known, such as a circular shape; a trapezoidal hood; a parabola with the lamp positioned at the focus of the parabola; an elliptical orientation where the lamp is positioned at one focus and the target area is at another focus (i.e., the major axis is vertical); and reflectors with ridges directly behind the lamp. Examples of prior reflectors are shown, for example, in U.S. Pat. Nos. 4,264,947 and 6,030,086.

FIG. 1 is a system diagram of a system for treating items using a flash lamp system with a UV-transmissive window, according to some embodiments of the present disclosure. FIG. 1 shows a UV system 10 with a UV flash lamp 12 coupled to a control system 16, a reflector 18, a UV-transmissive window 20, items 22, and a conveyor 23. Control system 16 controls, for example, the operation of UV flash lamp 12 including the frequency at which UV flash lamp 12 pulses per unit time and the intensity at which UV flash lamp 12 pulses. In some embodiments, reflector 18 surrounds a portion of UV flash lamp 12 to help direct the light output from UV flash lamp 12 in a desired direction through UV-transmissive window 20, the main portion of which is made of fused silica. The light output from UV flash lamp 12 passes through UV-transmissive window 20 to items 22 that are treated by the light output. Items 22 can be provided on conveyor belt 23, which can be stopped periodically during treatment or move continuously.

In some embodiments, items 22 may be optical memory disks with an adhesive that needs to be cured or items with a surface treatment that needs to be cured or annealed. Items 22 may also be food to be disinfected (as UV with wavelengths in the UV-C range are known to damage the DNA of pathogens), or a substrate with traces of a conductive ink with nanoparticles to be sintered to produce electrical circuits. This last example, of sintering a substrate with a conductive ink, will be used for purposes of description. In this case, the substrate can be made of a plastic film, or paper, or some other non-conductive material. Patterns of lines of conductive ink are formed on the substrate to create circuit paths. The substrate can be in individual pieces, as shown as items 22 in FIG. 1, or can be a continuous roll such that circuits are formed in a continuous substrate and separated using a later process.

FIG. 2 is a plan view of a system for treating circuit components using a single-cell flash lamp system, according to some embodiments of the present disclosure. FIG. 2 shows a lamp system including an elongated cylindrical flash lamp 30 and a substrate 32 with conductive electronic traces 34 and 36. A reflector, as described later herein, may often be used with the lamp system of FIG. 2, but is not shown here. Substrate 32 is shown moving in a direction from the left towards the right side of FIG. 2 and may be moved in that direction by a conveyor (not shown). The location of substrate 32 occupies a treatment area of the system and may be moved into and out of the treatment area manually by an operator, automatically by a conveyor, or by other processing means. Conductive electronic traces 34 and 36 may be made from a conductive ink with nanoparticles. As substrate 32 is moved left to right, either in a stop-and-start or a continuous manner, flash lamp 30 may flash a UV energy output at a set frequency (e.g., 3 flashes per second) and a set pulse duration (e.g., on the order of microseconds to milliseconds) as determined by an operator or a control system (not shown). In some embodiments, flash lamp 30 has a diameter "d" and a length "l". In embodiments of the system like that displayed in FIG. 2, there may be non-uniformities in the UV energy output, and therefore the energy delivered to substrate 32 can include higher and lower intensity areas within the total treatment area. Flash lamp 30 may produce a specific footprint of UV energy output onto substrate 32, made up of an area having width slightly larger than distance "d." Because of the dispersing nature of light produced from a single source, the intensity of light at the surface will have a peak intensity within the footprint of the flash lamp and that intensity will fall off towards zero quickly at locations further outside of the footprint. The UV energy output energy from lamp 30 sinters the ink used to create electronic traces 34 and 36 and fuses the particles. Sintering causes an increase in the pre-sintered conductivity of the electronic traces 34 and 36, as described in U.S. Patent Application Publication No. 2003/148024. In place of the circuit elements shown, the system in FIG. 2 may also be used for photographic processing, curing applications, or other applications where UV energy is applied to an item over large areas of treatment.

In some iterations of the system shown in FIG. 2, the system may have multiple lamps arranged in a row or in a two-dimensional array. Each lamp can be circular, elongated, spiral, or some other desired shape. The process of causing the lamp to flash for a desired duration, with a desired pulse frequency, is generally well known. The UV energy from a bare lamp, however, falls off rapidly as one moves away from points on the illuminated plane, described as the footprint of the lamp above, at minimum distance from the lamp. Small areas of uniformity exist in systems using multiple lamps, but the area of uniform UV energy output does not occupy an area that is much larger than the surface area of the lamps itself (e.g. outside of the footprint). For example, in the case of a cylindrical, elongated linear bulb with diameter "d" and length "l," the two-dimensional area of the bulb would be represented as l×d. In embodiments of the system described below, the area of uniform UV energy output is much larger than l×d, and is at least 10 times that area, or 10×l×w, or it may be more than 15, or 20, or 25 times the area of flash lamp 30. In the case of a cylindrical lamp with a diameter of 8 mm, the coverage area would be at least the length of the lamp, l×80 mm for a 10× coverage area; or for a 20× coverage area, l×160 mm. By use of suitable UV energy redirecting designs, as disclosed herein and explained in more detail with regard to FIGS. 3-6, the illumination across a larger defined area can be made uniform. In some embodiments, this is achieved by only using reflecting surfaces. Exclusive use of reflective surfaces minimizes the amount of output from a flash lamp lost to absorption or Fresnel reflection from any refractive medium used and is not susceptible to dispersion of colors due to varying refractive index with wavelength.

In some embodiments, the uniformity of UV energy incident upon a treated item, such as the circuit components 34, 36, should be such that the energy has not more than about a 5% variation throughout the coverage area. In other embodiments, the desired variation of an operator may range between about 2% and 10% variation, depending on the intended application or use. Variation across the coverage area may, for example, be measured as the comparison between the average illumination intensity across the entire treatment area and the average illumination intensity as measured at discrete sub-units of the treatment area. This uniformity can be measured, for example, with cyanotype paper that turns shades of blue in response to the UV flashes. The sheets can be scanned to determine the level of uniformity. The uniformity from the lamp system may also be measured using other indicator paper products or using area detectors to determine the intensity of incident UV light upon the treatment area.

FIG. 3a is a side view of a system for treating items using a flash lamp system with a flash lamp reflector cell having an elliptical reflector cap, according to some embodiments of the present disclosure. FIG. 3a shows a flash lamp 39 and a reflector cell 41 positioned over a conveyor 49. Reflector cell 41 includes an elliptical reflector cap 43 and shroud walls 45, 47 (also referred to herein as "components" of reflector cell 41). Conveyor 49 has a width (not shown) that extends along the plane of the conveyor 49 into FIG. 3a such that distance 51 between shroud walls 45 and 47 defines a coverage area quantified as the width of conveyor 49 times the distance 51. Conveyor 49 may be configured to transport items and may be replaced by other processing means including, for example, manual movement by an operator. Reflector cell 41 may also include additional shroud walls, such as walls perpendicular to walls 45 and 47 (not shown) that completely enclose the coverage area of conveyor 49 over distance 51. Reflector cell 41 may include shroud walls have a horizontal dimension, measured in the same direction as distance 51, a vertical dimension, measured between conveyor 49 and flash lamp 39, and a longitudinal dimension, measured along the same longitudinal axis of flash lamp 39 (e.g. into the page as depicted in FIG. 3a). In some embodiments, the longitudinal dimension of reflector cell 41 may be the same distance as the width of conveyor 49. Shroud walls 45 and 47 are on either side of the coverage area and extend downward and substantially perpendicular to the conveyor 49. Shroud walls 45 and 47 may extend most of the way to the conveyor 49 such that minimal space exists between shroud walls 45, 47 and conveyor 49. At least one of the benefits of this configuration is that minimal light from the environment may enter the internal space of reflector cell 41, allowing for precise delivery of UV energy output from flash lamp 39 to the surface of conveyor 49 or items treated thereon. In some embodiments, reflector cell 41 may include a window (not shown) between flash lamp 39 and conveyor 49, similar to that described above with respect to FIG. 1

In FIG. 3a, elliptical reflector cap 43 is a portion of an ellipse that extends from shroud wall 45 over flash lamp 39 to shroud wall 47. The ellipse corresponding to elliptical reflector cap 43 has two foci: f1, which is a location, but not a physical item, where flash lamp 38 may be placed, and a second focus f2. The major axis created by the locations of the two foci is perpendicular to a line from the flash lamp 39 to the items being treated, e.g., horizontal in the depicted orientation. Flash lamp 39 is placed at focus f1 so that the UV energy output from flash lamp 39 reflects from the elliptical reflector cap 43 and appears at conveyor 49 as if the UV energy output is emanating from one of two virtual sources, lying in distinct planes above the true source, in addition to the light output physically emanating from flash lamp 39 itself. A first virtual source 51 will result from the reflection of flash lamp 39 in elliptical reflector cap 43 at a location sufficiently close to above the first focal point f1. A second virtual source 53 will result from the reflection of the flash lamp 39 in elliptical reflector cap 43 at a location sufficiently close to above the second focal point f2. The effect is to make each individual UV energy source, e.g. flash lamp 39, behave as if three separate UV energy sources, although two of the virtual sources lie in one plane somewhat farther from the illuminated plane, while the third literal source lies at the first focal point f1. Flash lamp 39 may also be placed at focal point f2, wherein the virtual images described above would reverse orientation between their locations above the first and second focal points, f1 and f2.

Figure 3B:
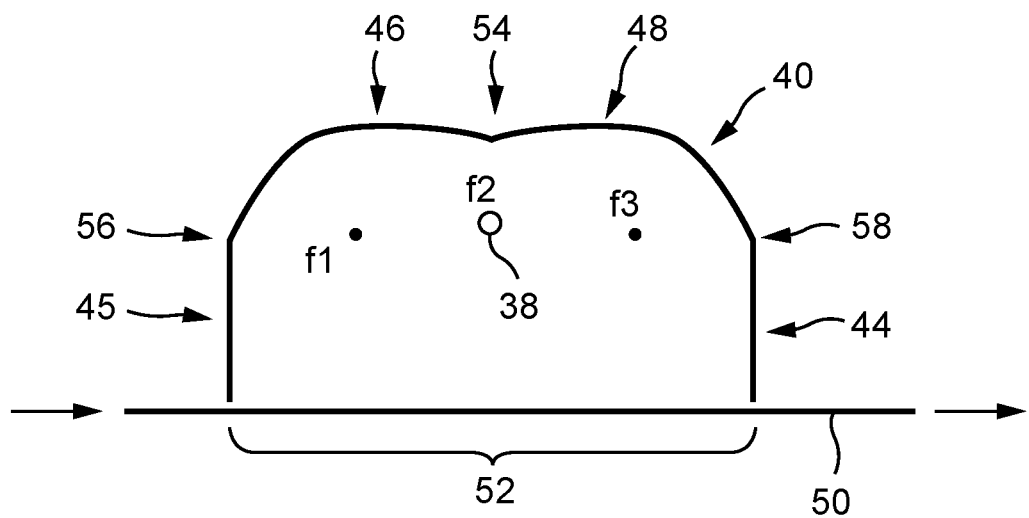
FIG. 3b is a side view of a system for treating items using a flash lamp system with a flash lamp reflector cells made of multiple elliptical portions, according to some embodiments of the present disclosure.

FIG. 3b is a side view of a system for treating items using a flash lamp system with a flash lamp reflector cell made of multiple elliptical portions, according to some embodiments of the present disclosure. FIG. 3b shows a flash lamp 38, and a reflector 40 cell positioned over a conveyor 50. Reflector cell 40 includes shroud walls 42 and 44 as well as elliptical reflector caps 46 and 48 (also referred to herein as "components" of reflector cell 40). Conveyor 50 has a width (not shown) that extends along the plane into FIG. 3b such that a distance 52 between shroud walls 42 and 44 defines a coverage area quantified as the width of conveyor 50 times the distance 52. Conveyor 50 is configured to transport items (not shown). Other processing means may be used in place of conveyor 50 including moving items manually by an operator or by other processing means. Reflector cell 40 may also include additional shroud walls (not shown) that completely enclose the coverage area of conveyor 50 over distance 52. Reflector cell 40 may include shroud walls having a horizontal dimension, measured in the same direction as distance 52, a vertical dimension, measured between conveyor 50 and flash lamp 38, and a longitudinal dimension, measured along the same longitudinal axis of flash lamp 38 (e.g., into the page as depicted in FIG. 3b). In some embodiments, the longitudinal dimension of reflector cell 40 may be the same distance as the width of conveyor 50. Shroud walls 42 and 46 are on either side of the coverage area and extend downward and substantially perpendicular to the conveyor 50. Shroud walls 42 and 46 may extend most of the way to the conveyor 50 such that minimal space exists between shroud walls 42, 46 and conveyor 50. One of the benefits of this configuration is that minimal light from the environment may enter the internal space of reflector cell 40, allowing for precise delivery of UV energy output from flash lamp 38 to the surface of conveyor 50 or items treated thereon.

In some embodiments, the shroud walls 42 and 46 are planar walls made of substantially nearly perfect specular mirrors, with very high reflectivity and with substantially planar and mechanically stable walls. Due to the distance between the flash lamp 38 and the conveyor 50, the UV energy output intensity will decrease while it propagates from the flash lamp 38 and is also affected by the increasing number of reflections. However, by that time the UV energy output appears to be coming from ever more distant virtual lamps behaving as a homogenous sheet of light output incident on a treatment area. In some embodiments, the components of reflector cell 40 may be constructed using a single piece of material. In other embodiments, the components of reflector cell 40 may be coupled using clips, buckles, brackets, screws, or other fasteners. In some embodiments, reflector cell 40 may include a window (not shown) between flash lamp 38 and conveyor 50, similar to that described above with respect to FIG. 1

Elliptical reflector caps 46 and 48 are each portions of different ellipses. Elliptical reflector cap 46 is a portion of an ellipse that extends from point 54 directly above flash lamp 38 to point 56 where it meets the shroud wall 42. The ellipse corresponding to elliptical reflector cap 46 has two foci: f1, which is a location, but not a physical item, and a second f2 where flash lamp 38 may be placed. A major axis created by the locations of the two foci is perpendicular to a line from the flash lamp 38 to the items being treated. Elliptical reflector cap 48 is a portion of an ellipse that extends from point 54 directly above flash lamp 38 to point 58 where elliptical reflector cap 48 couples to shroud wall 44. The ellipse corresponding to elliptical reflector cap 48 has two foci, the first of which is found at location f2 in a concurrent location with that formed by flash lamp 38 and elliptical reflector cap 46 focus f2. The second focus of elliptical reflector cap 48 is found at f3, which is another non-physical location. The distance between f1 and f2 is equal to the distance between f2 and f3, and as shown, foci f1, f2, and f3 are oriented perpendicular to the direction from lamp 38 to the items to be treated.

In some embodiments, the elliptical reflector caps 46, 48 redirect the UV energy output emitted from flash lamp 38, which requires one or more reflections before it illuminates the treatment area defined by distance 52 on conveyor 50. In this way, the UV energy output "fills in" the places where the illumination from the UV energy output of flash lamp 30 is below a necessary threshold for treating items. Additionally, the components of reflector cell 40 illuminate conveyor 50 without materially saturating places that are already sufficiently covered by the direct illumination from flash lamp 38 and do so in such a way that the variations in illumination are precisely compensated for. The uniform illumination of a treatment surface is supported by the understanding that, from a sufficiently great distance, UV energy output from a single source may appear as a uniform distribution of UV energy detection at that location sufficiently far away. There may be small variations in the illumination along a direction perpendicular to the longitudinal axes of the sources, but with increasing distance, anomalies in UV energy distribution decrease rapidly until they are sufficiently small and do not affect the application to a treatment area, described in detail below. In some embodiments, the reflector cell functions such that a single or finite number of lamps appear at the illuminated plane as if provided by an infinitely wide array of equally-spaced, infinitely long UV energy sources.

In some embodiments, reflector cell 40 produces a treatment area that is at least a factor of 10 larger than the surface area of the flash lamp, as described above. Additionally, the treatment area canvassed by reflector cell 40 is substantially uniform. The reflections in the system produce the appearance of an infinite number of UV energy sources. Multiple reflector cells 40 may be used in conjunction to treat an area having a total width equal to the sum of each individual reflector cell's 40 width.

In some embodiments, the reflector can be manufactured in one of a number of ways, e.g., with a highly reflective sheet metal, or it can be formed by starting with a block of material from which material is removed to form the contours, or 3D printing techniques can be used.

Figure 4:
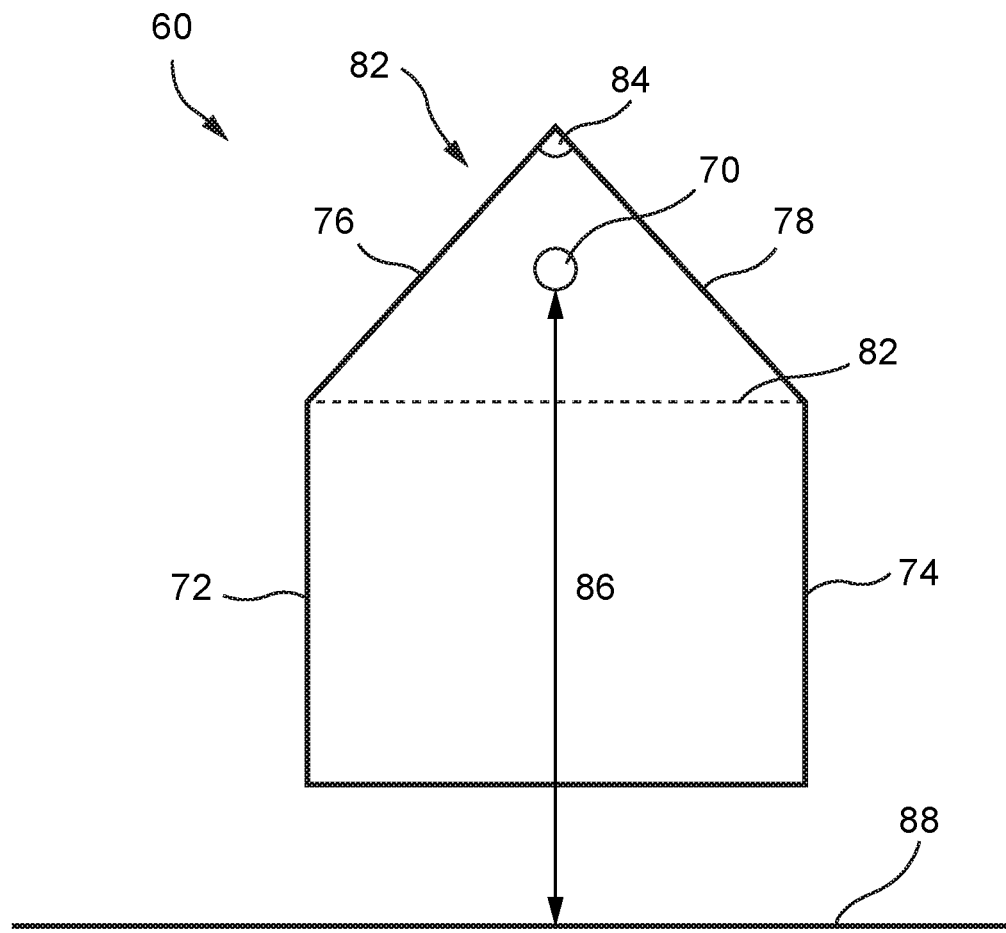
FIG. 4 is a side view of a system for treating items using a flash lamp system with a single angular flash lamp reflector cell, according to some embodiments of the present disclosure.

FIG. 4 is a side view of a system for treating items using a flash lamp system with a flash lamp angular reflector cell, according to some embodiments. FIG. 4 shows an angular reflector cell 60 that includes a flash lamp 70, angular reflector cap 82, shroud walls 72 and 74, and a processing surface 88. Processing surface 88 may comprise a conveyor, as described above in FIGS. 1-3. Angular reflector top 82 includes upper angled pieces 76 and 78 that extend upwardly at an angle relative to the vertical direction and meet at an angle 84 above flash lamp 70. This forms a V-shaped cross-section. In some embodiments, the angle 84 of the V-shape between upper angled pieces 76 and 78 is a right angle. The reflector cap and shroud, along with the conveyor, generally trace out a "home plate" shape in cross section. Flash lamp 70 has a vertical position 86 that is above a line 80 between the tops of the shroud walls 72, 74. In some embodiments, a window (not shown) may be placed along with line 80, similar to that described above with regard to FIG. 1. In some embodiments, the angled reflector cell 60 may include additional shroud components (not shown) such that an area exists within the angled reflector cell 60 that is enclosed on five sides, with an opening over processing surface 88. In some embodiments, the angular reflector cell may include a window (not shown) similar to that described above with respect to FIG. 1

In some embodiments, the configuration of the angled reflector cell provides the virtual appearance as if UV energy output from flash lamp 70 originates from multiple UV energy sources and multiple distances from items (not shown) being treated on a processing surface 88 by UV energy output from flash lamp 70. A second distance between the flash lamp 70 and the portions of angular reflector cap 82, as well as the widths of the portions of angular reflector cap 82 are chosen so that the UV energy output from flash lamp 70 reflects from the angular reflector cap 82 and appears at processing surface 88 as if the UV energy output is emanating from one of three virtual sources, lying in two distinct planes above the true source in addition to the light output physically emanating from flash lamp 70 itself. A first virtual source (not shown) will result from the reflection of flash lamp 70 in upper angled piece 76. A second virtual source (not shown) will result from the reflection of the flash lamp 70 in upper angled piece 78. Finally, a third virtual source (not shown) will result from the reflection of flash lamp 70 at the connection of upper angled pieces 76, 78 directly above flash lamp 70. The effect is to make each individual UV energy source, e.g. flash lamp 70, behave as if four separate UV energy sources, although three of the virtual sources lie in one plane somewhat farther from the illuminated plane, while the third virtual source lies in yet another plane, even farther from the illuminated plane.

In some embodiments, the angular reflector cell uses only surfaces as flat as mechanically possible with present manufacturing techniques that meet at right angles or any other angle that is a multiple of 45 degrees. Such angular reflector cell covers may be easier and less expensive to construct than, for instance, elliptical surfaces. In some embodiments, upper angled pieces 76, 78 may be oriented at angles relative to the horizontal (e.g. relative to the processing surface or line 80), where use of the term "positive" angle indicates an angle measured counterclockwise from a relative starting point. Conversely, the term "negative" angle indicates an angle measured clockwise from a relative starting point. For example, as shown in FIG. 4, upper angled piece 76 may be oriented at a positive angle of 45 degrees as measured relative to the horizontal (e.g. line 80). Additionally, upper angled piece 78 may be oriented at a negative angle of 45 degrees as measured relative to the horizontal.

As described above with regard to FIG. 3b, reflecting the UV energy output from a flash lamp like flash lamp 70 employs the process of effectively multiplying the flash lamp 70 output. That multiplication may result from virtual sources created by the reflective surfaces of angled reflector cap 82 and shroud walls 72, 74. UV energy that emanates downward from flash lamp 70, or from the virtual line sources generated by the angled reflector cap 82, propagates downward to a treatment area defined by the distance between shroud walls 72, 74 and the width of processing surface 88. UV energy output from flash lamp 70 may also reflect once or multiple times off of shroud walls 72, 74 before reaching the treatment area on processing surface 88. Shroud components (not shown) may be provided perpendicular to the longitudinal axis of the flash lamp 70 such that flash lamp 70 appears to virtually extend along an infinitely long line. Shroud walls 72, 74, placed at either end of the processing surface 88 create a virtual image of the flash lamp 70 that appears to extend beyond the location of the shroud walls 72, 74 on either proximal end of the angled reflector cell. Shroud walls 72, 74 may be parallel to the longitudinal axis of flash lamp 70 making the effectively tripled number of sources act as if they extend for an infinite distance along both directions perpendicular to the axis.

Figure 5:
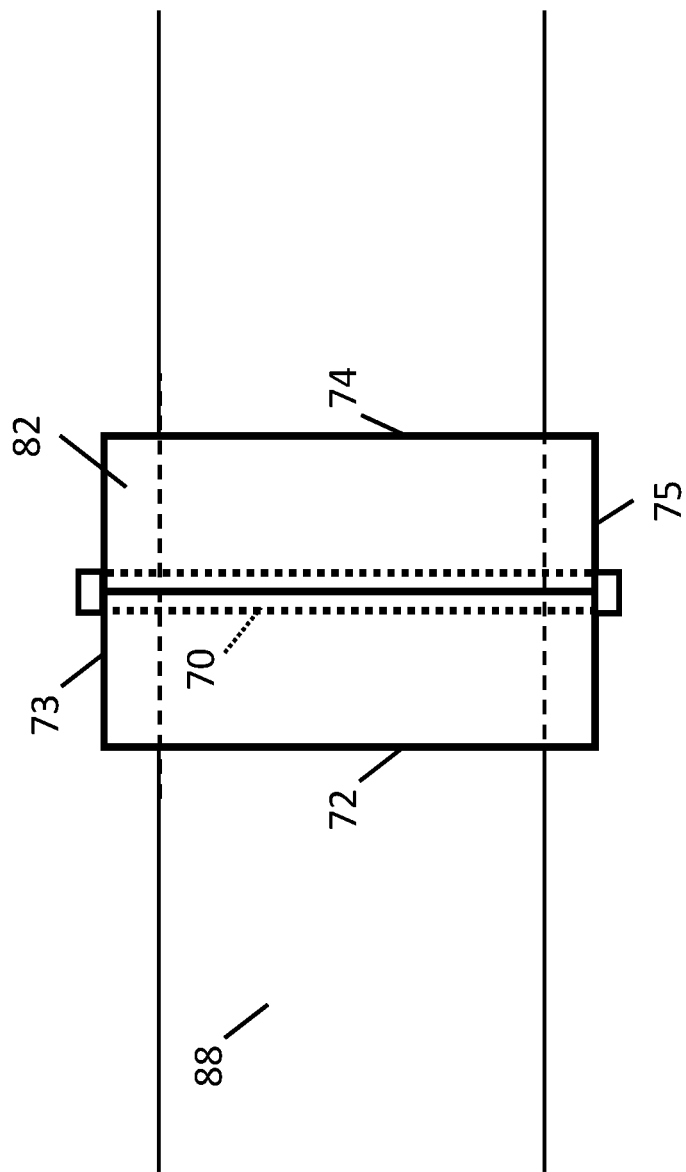
FIG. 5 is a top view of a system for treating items using a flash lamp system with a singular flash lamp angular reflector cell, according to some embodiments of the present disclosure.

FIG. 5 is a top view of a system for treating items using a flash lamp system with a single flash lamp in an angular reflector cell of the type shown in FIG. 4, according to some embodiments of the present disclosure. FIG. 5 shows flash lamp 70, processing surface 88, and shroud walls 72, 73, 74, 75. In some embodiments, shroud walls 72 and 74 are substantially parallel to each other, and shroud walls 73 and 75 are substantially parallel to each other. Shroud walls 72, 73, 74, 75 are coupled such that they form a box that defines a treatment area of processing surface 88 to be uniformly illuminated. Shroud walls 72, 73, 74, 75 produce a "hall of mirrors" effect, making the flash lamp 70, and the virtual counterparts created by angled reflection cap 82, appear to extend on into infinity along all directions, so that it will resemble an infinitely long and wide UV energy source that is parallel to the conveyor surface at a fixed vertical distance, as described above. In some embodiments, shroud walls 72, 74 are coupled to shroud walls 73, 75 such that an angle between their connections forms a right angle. In some embodiments, each of shroud walls 72-75 are perpendicular to processing surface 88. Because there will be multiple reflections from the mirrored surfaces on the interior of shroud walls 72-75 the reflectivity of the interior of shroud walls 72-75 may be as high as possible with present manufacturing techniques as required for the wavelength of UV energy emitted by flash lamp 70.

The longer the shroud walls are, the more uniform will be the illumination at the desired plane. However, the longer the walls, the more reflections there will be, each exacting a fraction of the incident UV energy. Also, the longer the shroud walls, the larger the overall device will be. A tradeoff analysis must be made to balance uniformity against overall illumination and size. In some embodiments, the shroud should be at least 2-3 times the cell width "w" for uniformity down to the single digit percentage range, as described above. Shorter shrouds can be used at the expense of this level of uniformity.

In some embodiments, shroud walls 72-75 may be highly specular reflectors. Shroud walls 72-75 may be highly reflective or textured, they can be made of metal, such as aluminum with a magnesium coating, e.g., a product known as Coilzak, or other covered materials, such as a material with a laminate or covering of expanded PTFE. In some embodiments, the interior of angled reflector cap 82 may be textured and not too reflective. In some embodiments, reflector cell 82 may be symmetric such that the spacing of reflector elements results in virtual images of the flash lamp that are equidistant from one another, from the perspective of the illuminated processing surface 88. If the symmetry in those non-limiting embodiments is broken (e.g. different sized components, improper angles between adjacent components) the illumination of processing surface 88 may not be uniform.

Figure 6:
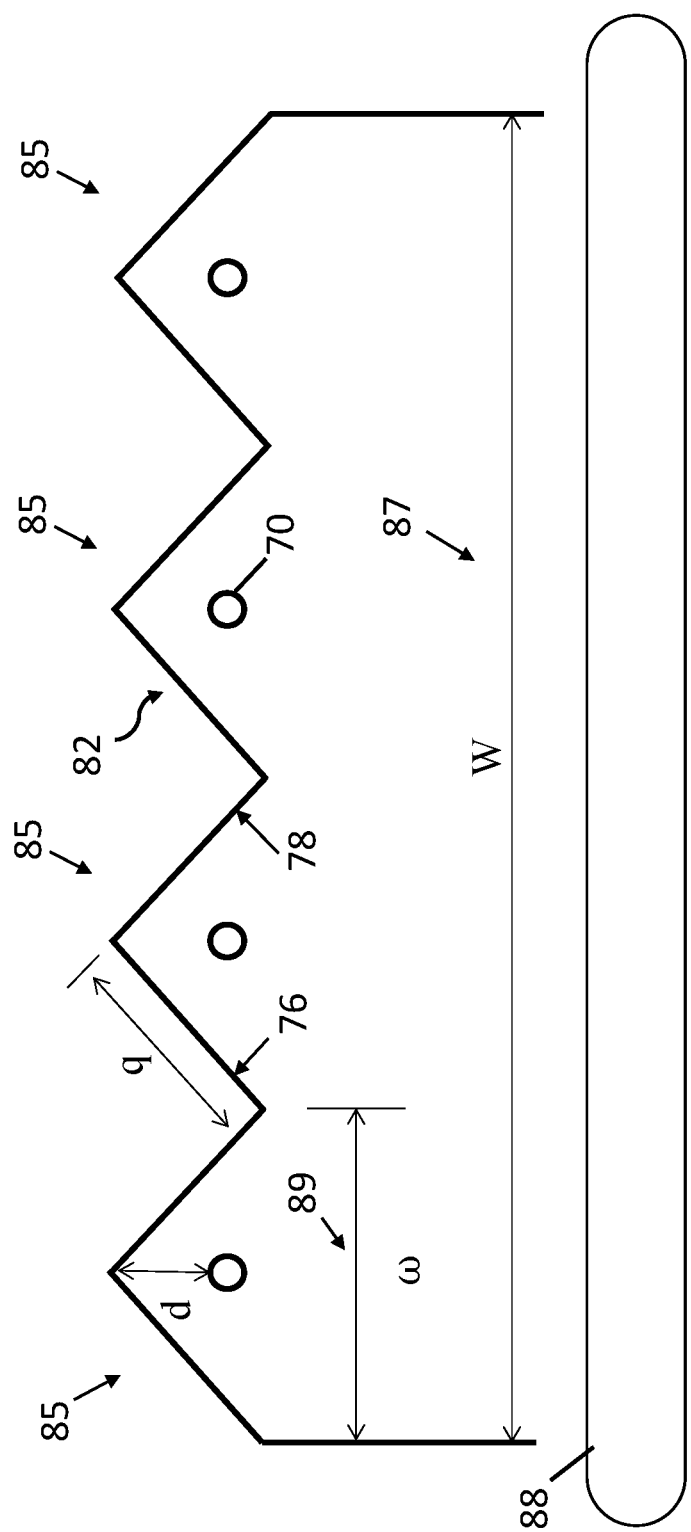
FIG. 6 is a side view of a system for treating items using a flash lamp system with multiple angular flash lamp reflector cells, according to some embodiments of the present disclosure.

FIG. 6 is a side view of the system for treating items using a flash lamp system with multiple flash lamp angular reflector cells, according to some embodiments. FIG. 6 is substantially similar in many ways to the single-cell system shown in FIGS. 4 and 5 but differs by combining multiple single cells into an implemented system. FIG. 5 shows a plurality of angled reflector cells 85, each including angled reflector cap 82 made of upper angled pieces 76, 78, and a plurality of flash lamps 70 above a processing surface 88 having a treatment area 87 with width "W." Using the dimensions identified in FIG. 6, for example, multiple flash lamp angular reflector cells 85 may cover N regions with an overall width of the treatment area 87 to be illuminated having a width W. As shown, each angled reflector cell 85 has a width 89 (notated as w) calculated as a division of the treatment area 87 by the number of desired cells W/N.

In some embodiments, as described in FIG. 4, each angular reflector cell 85 may include an angular reflector cap 82. Angular reflector cap 82 includes upper angled pieces 76, 78 coupled to form an angle, made possible by each of upper angled pieces 76, 78 having a length q. Length q is calculated such that each of upper angled pieces 76, 78 have a length given by $$q = \frac{w}{\sqrt{2}}$$

In some embodiments, upper angled pieces 76, 78 are placed at an angle of 45° as measured relative to the angle of the plane to be illuminated. A bottom edge of each of upper angled pieces 76, 78 may align such that the plane between two pieces bottom edge meet should be parallel to processing surface 88, and an apex of angular reflector cap 82 should be a distance "d" from the flash lamp 70. In some embodiments, lengths q of both upper angled pieces 76, 78 are the same. In some embodiments, distance "d" may be calculated as one fourth of width 89, such that d=w/4. Distance "d" may be above flash lamp 70 in the direction opposite that of the treatment area 87. In some embodiments, each of the flash lamps 70 may have a corresponding angular reflector cap 82 above it. In some embodiments, the multiple angular reflector caps 82 may be constructed using a single piece of material.

Figure 7:
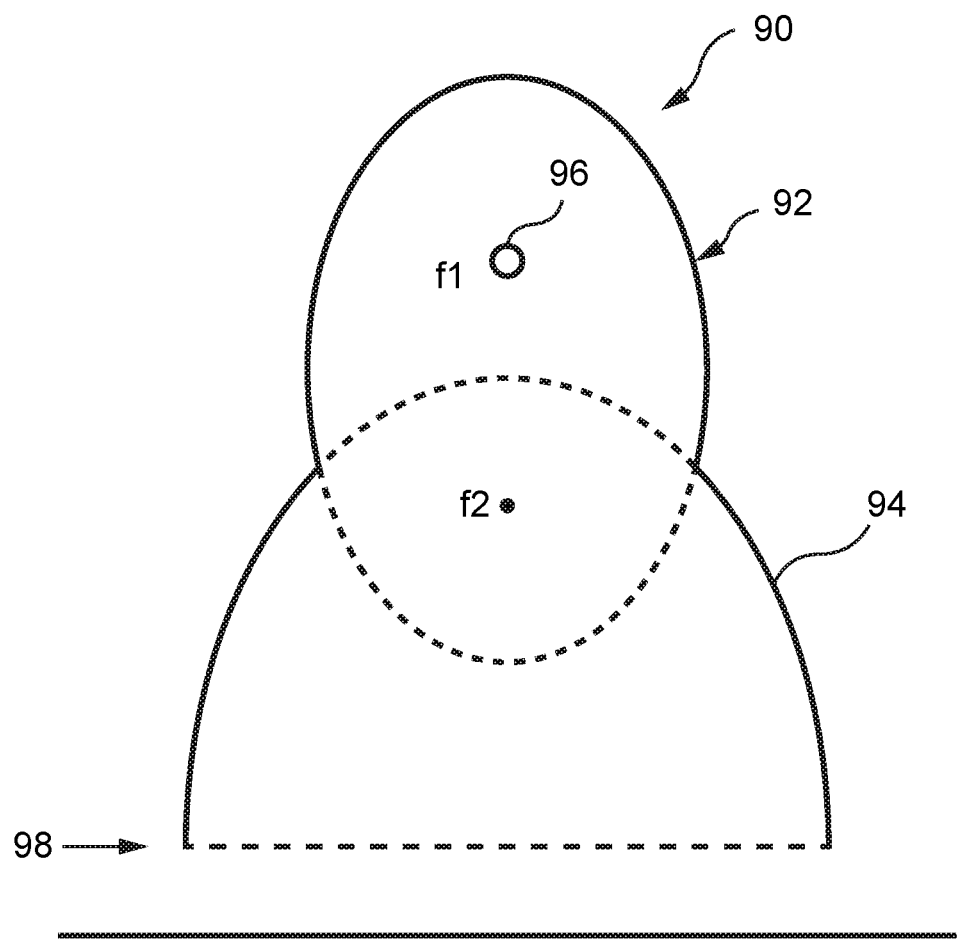
FIG. 7 is a side view of a system for treating items using a flash lamp system with multiple, overlapping circular segment reflector cells, according to some embodiments of the present disclosure.

FIG. 7 is a side view of a system for treating items using a flash lamp system with multiple, overlapping circular segment reflector cells, according to some embodiments of the present disclosure. FIG. 7 shows an elliptical reflector cell 90 including an elliptical portion 92 and a parabolic portion 94. The elliptical portion 92 has a vertically oriented major axis created by the virtual connection of a first focus, f1, and a second focus, f2. A flash lamp 96 is located at first focus, which is above the second focus. The elliptical portion 92 is coupled to parabolic portion 94. Parabolic portion 94 has a focus that is in the same position as the second elliptical focus, f2, of the elliptical portion 92. In some embodiments, a window (not shown), like that described with respect to FIG. 1, may be placed at the bottom of the parabolic portion 94 along a line 98. In some embodiments, the UV energy output of flash lamp 96 within elliptical reflector cell 90 is uniform across a 10× or more coverage area compared to the surface area of flash lamp 96, although there may be some increase along the outer edges of a wider coverage area.

In the discussion above, it has been generally assumed that the lamp would be a single cylindrical lamp, but a spiral, helical, or U-shaped lamp could also be used. As with the cylindrical configuration, a minimum of 10× coverage area compared to the area of the outline of the lamp, or even 15×, 20×, or 25× coverage area is desired. The terms "above" and "below," and "over" and "under," are used to indicate relative positioning. A lamp could be provided above or below a conveyor relative to a gravitational direction, but for purposes here, the lamp is considered over or above the conveyor.

The inventions described here thus include reflectors, UV energy systems with reflectors, methods for manufacturing a reflector, and methods for using reflectors in a UV energy system. It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods, and systems for carrying out the several purposes of the disclosed subject matter. It is important, therefore, that the claims be regarded as including such equivalent constructions insofar as they do not depart from the spirit and scope of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter, which is limited only by the claims which follow.

The invention claimed is:

1. A system for providing ultraviolet (UV) energy to items on a processing surface, the system comprising:
   a lamp positioned over the processing surface to provide UV energy to the processing surface; and
   a reflector cell positioned to cause UV energy emitted from the lamp in a direction away from the processing surface to be reflected toward the processing surface, the reflector cell including:
  a reflector cap positioned above the lamp, wherein the reflector cap comprises a first elliptical shape with a major axis along a first line parallel to the processing surface and perpendicular to a second line from the lamp to the processing surface, the lamp being positioned at a first focus of the elliptical shape, and
  a shroud extending downwardly from the reflector cap toward the conveyor, the shroud having a vertical dimension, a longitudinal dimension, and a horizontal dimension along the direction of the conveyor, the horizontal dimension and the longitudinal dimension defining a treatment area on the conveyor,
  the lamp configured to deliver energy to the treatment area, wherein the reflector cap and the shroud are configured such that the delivered energy to the processing surface is substantially uniform over the treatment area.

2. The system of claim 1, wherein the lamp includes at least one flash lamp and the energy in the treatment area is substantially uniform to within 5%.

3. The system of claim 2, wherein the processing surface is defined by a conveyor.

4. The system of claim 1, wherein the reflector cap and the shroud define and enclose a treatment volume, the reflector cap and the shroud having a reflective material along their respective interior surfaces facing the treatment area.

5. The system of claim 1, wherein the reflector cap includes a second elliptical shape with a major axis along the first line, the second elliptical shape having a first focus co-located with the first focus of the first elliptical shape, and a second focus of the second elliptical shape being spaced from the first focus and from a second focus of the first elliptical shape along the first line.

6. The system of claim 5, wherein the second elliptical shape comprises at least one section of one or more ellipses.

7. The system of claim 1, wherein the reflector cap includes a second focus below the first focus, wherein the shroud has a parabolic shape with a focus co-located with the second focus of the reflector cap.

8. The system of claim 1, further comprising a UV-transmissive window positioned between the lamp and the processing surface.

9. The system of claim 1, wherein the first elliptical shape comprises at least one section of one or more ellipses.

10. A system comprising:
  at least one ultraviolet (UV) energy lamp positioned above a processing surface, wherein the plane of the processing surface defines a first direction, and the direction from the lamp to the processing surface is a second direction perpendicular to the first direction; and
  a reflector cell positioned to cause UV energy emitted from the lamp in a direction away from the processing surface to be reflected toward the processing surface, the reflector cell including;
  a reflector cap positioned above the lamp and away from the processing surface, the reflector cap having first and second planar panels that extend away from the processing surface at an angle relative to the second direction and meet at a location above the lamp and form a V-shaped cross section, and
  a shroud having at least a third panel extending downwardly from the first panel toward the conveyor, and a fourth panel extending toward the processing surface and parallel to the third side, the lamp providing energy to the processing surface in a treatment area below the first and second sides and bounded by the third and fourth panels.

11. The system of claim 10, wherein the lamp includes a flash lamp.

12. The system of claim 10, wherein the reflector cap and the shroud define a treatment volume, the reflector cap and the shroud including a reflective material along interior surfaces facing the treatment volume.

13. The system of claim 10, wherein the first and second panels intersect such that the V-shape is approximately 90 degrees.

14. The system of claim 10, wherein the processing surface includes a conveyor, the system further comprising a UV-transmissive window positioned between the lamp and the conveyor.

15. The system of claim 10, wherein the fourth panel extends downwardly from the second panel, such that the first, second, third, and fourth panels define a home plate shape in cross-section.

16. The system of claim 10, further comprising a second lamp and a second reflector cap having fifth and sixth planar panels that that extend away from the processing surface at an angle relative to the second direction and meet at a location above the lamp and form a second V-shaped cross section.

17. The system of claim 10, wherein the first planar panel and the second planar panel extending upwardly away from the processing surface and at about a positive and negative 45 degree angle, respectively, relative to the processing surface, the first and second planar panels intersecting above the lamp such that an angle between the first planar panel and the second planar panel is approximately 90 degrees.

18. The system of claim 17, wherein the lamp includes a first lamp and a second lamp spaced apart, wherein the first and second planar panels extend over the first lamp, the system further comprising a third planar panel and a fourth planar panel, the third planar panel and the fourth planar panel extending upwardly away from the processing surface and at about a positive and negative 45 degree angle, respectively, relative to the processing surface, the third and fourth planar panels intersecting above the second lamp such that an angle between the third planar panel and the fourth planar panel is approximately 90 degrees.

19. A system comprising:
  at least one ultraviolet (UV) energy lamp positioned above a planar processing surface, wherein a direction from the lamp to the processing surface is a first direction perpendicular to the processing surface; and
  a reflector cell positioned to cause UV energy emitted from the lamp in a second direction away from the processing surface to be reflected toward the processing surface, the reflector cell including,
  a reflector cap positioned above the lamp and away from the processing surface, wherein the reflector cap includes a first elliptical portion that defines a first elliptical shape with a major axis parallel to the processing surface and perpendicular to the first direction, wherein the lamp is located at one focus of the first elliptical portion, and
  a shroud extending from the reflector cap toward the processing surface.

20. The system of claim 19, further comprising a second elliptical portion having a major axis co-linear with the major axis of the first elliptical portion, wherein the lamp is located at a first focus of the second elliptical portion, and a second focus of the second elliptical portion is spaced from both foci of the first elliptical portion.

21. The system of claim 19, wherein the shroud includes first and second panels that are spaced apart and extend from the reflector cap toward the processing surface, the spacing of the first and second panels defining a dimension of a treatment area for the UV energy.

\* \* \* \* \*